(12) United States Patent
Brush

(10) Patent No.: US 10,755,197 B2
(45) Date of Patent: Aug. 25, 2020

(54) RULE-BASED FEATURE ENGINEERING, MODEL CREATION AND HOSTING

(71) Applicant: CERNER INNOVATION, INC., Kansas City, KS (US)

(72) Inventor: Ryan Alan Brush, Overland Park, KS (US)

(73) Assignee: CERNER INNOVATION, INC., Kansas City, KS (US)

(*) Notice: Subject to any disclaimer, the term of this patent is extended or adjusted under 35 U.S.C. 154(b) by 789 days.

(21) Appl. No.: 15/152,973

(22) Filed: May 12, 2016

(65) Prior Publication Data

US 2017/0330102 A1 Nov. 16, 2017

(51) Int. Cl.
- *G06N 20/00* (2019.01)
- *G06F 19/00* (2018.01)
- *G06N 5/02* (2006.01)

(52) U.S. Cl.
CPC ......... *G06N 20/00* (2019.01); *G06F 19/3456* (2013.01); *G06N 5/025* (2013.01)

(58) Field of Classification Search
CPC ..... G06F 19/3456; G06F 19/00; G06N 20/00; G06N 99/005; G06N 5/025
See application file for complete search history.

(56) References Cited

U.S. PATENT DOCUMENTS

| | | | | |
|---|---|---|---|---|
| 2003/0208514 A1* | 11/2003 | Yang | ...................... | G06F 3/0481 708/160 |
| 2007/0022066 A1* | 1/2007 | Goldstein | ................ | G06N 5/02 706/20 |
| 2008/0101705 A1* | 5/2008 | Mohamed | .......... | G06K 9/00885 382/224 |
| 2011/0224565 A1* | 9/2011 | Ong | ..................... | A61B 5/4824 600/509 |
| 2014/0101076 A1* | 4/2014 | Martin | .................. | G06F 21/604 706/11 |
| 2016/0004979 A1* | 1/2016 | Getchius | ............... | G06F 19/328 706/12 |
| 2017/0220947 A1* | 8/2017 | Tariq | .................. | G06Q 30/0202 |

OTHER PUBLICATIONS

Sun et al., "Combining Knowledge and Data Driven Insights for Identifying Risk Factors using Electronic Health Records", Nov. 3, 2012, AMIA Annu. Symp. Proc., pp. 901-910 (Year: 2012).*

Xu, "Mapping Snomed CT to ICD-10-CM", Jan. 2016, PhD Dissertation for Rutgers School of Health Related Professions, pp. 1-134 (Year: 2016).*

* cited by examiner

*Primary Examiner* — Kamran Afshar
*Assistant Examiner* — Brent Johnston Hoover
(74) *Attorney, Agent, or Firm* — Shook, Hardy & Bacon LLP

(57) ABSTRACT

Methods, systems, and computer-storage media are provided for generating and populating a feature catalog for use in predictive modeling applications. The feature catalog may be populated with features extracted from data warehoused in a nested, hierarchical data structure. Extraction of features may result from applying a set of rules-based algorithms to warehoused data. Updated features may be extracted from a queue of data updates by applying the same rules-based algorithms. Predictions of future outcomes may be generated by applying predictive models to features.

19 Claims, 5 Drawing Sheets

RULE-BASED FEATURE ENGINEERING, MODEL CREATION AND HOSTING

BACKGROUND

The present disclosure pertains to the field of data processing, particularly with regard to data structure design, machine learning, and predictive modeling. The novel aspects of this disclosure are equally as applicable to techniques used in the fields of academic research and administrative agency studies as they would be in the commercial context. The present disclosure represents an improvement to the field of data science.

In recent years, the generation of enormous pools of data has presented an unprecedented opportunity for applying computing power to the task of creating ever more accurate models of the physical world in which we live. However, the enormous depth and complexity of the data sets generated, colloquially referred to as "Big Data", has proven to render traditional data processing applications inadequate.

The challenges presented by Big Data can broadly be separated into two categories: tasks related to data management and maintenance and tasks related to data analysis and interpretation. These tasks are generally addressed by two separate and distinct groups of specialists: software engineers, primarily addressing data management and maintenance, and data scientists, focused on analysis and interpretation. Software engineers generate applications to curate the lifecycle of data; from receiving the data, to cataloging, addressing and storing the data within data structures, to retrieving data in response to a query or search, and eventually removing data when it is no longer accurate or valuable. Data scientists, on the other hand, can generate predictive models by applying tools, such as predictive modeling and machine learning applications, which can be useful in, for instance, assessing risks of adverse future outcomes based on current conditions. It is anticipated that demand for predictive modeling will only continue to rise.

The predictive models generated by data scientists can take many forms, including algorithms, matrices, and equations. Predictive modelling may include applying a variety of statistical techniques for identifying possible future outcomes. While the precision of predictive models can depend greatly on the complexity of the model and the number of parameters included, the accuracy of these predictive models are highly dependent on the initial sample size of applicable data that the model is applied against. This generally requires access to large stores of data, but it also requires that the data be structured and formatted to be accessible by the software tools utilized by the data scientists, which often require tabular or comma-delineated data sets.

From the software engineering perspective, satisfying the requirements of the data scientist creates additional demands on their data curation role. Though the data is unquestionably valuable to the data scientist for generating their predictive models, data is often primarily maintained for other record-keeping or warehousing purposes, and the structures in which that data is stored is generally geared toward those other purposes. Data warehousing is generally focused on maintaining data with a high degree of detail and granularity to ensure that the stored data is faithful to its source.

The structures in which data is stored or warehoused may have a significant impact on how effectively that data can be accessed in response to particular types of queries. While certain data structures, such as highly nested, hierarchical structures, are better suited for long term storage of raw data relating to distinct and separate records, other data structures, such as comma-delineated files and tables, are better at facilitating rapid access of features in the data for research and analysis.

The competing design requirements between the data warehousing and data analysis paradigms tends to create a bottleneck in the continued development of predictive modeling using Big Data sets. Producing a system which incorporates a solution suitable both for the needs data scientists have in testing and deploying their models and which also satisfies the record-keeping requirements of software engineers generally demands a large collaborative effort between data scientists and software engineers, and generally results in a bespoke solution which has little applicability, if any, to predictive models other than the one for which it is designed, requiring a new solution to be developed for each new model.

Complicated predictive models typical require leveraging a large engineering effort and deep technical expertise to provide the necessary data to test, verify and host the model. When attempting to do predictive modeling at scale, data scientists encounter problems relating to the data structure in which the data is warehoused.

Predictive models generally must be verified in order to demonstrate their value. Verification involves populating the model with empirical data, running the model to produce predictions, and comparing the predicted outcomes with empirically determined true outcomes. The verification process may be applied in an open-ended manner, wherein a large number of disparate features are analyzed for their comparative predictive power.

Predictive modeling/machine learning protocols, such as predictive model markup language (PMML), typically receive data library files in the form of a table or comma-delimited file. Data warehoused in a star-schema or a more sophisticated, domain-specific structure is not directly usable by machine learning protocols, not only because representing data to such high fidelity can make analysis of the data unwieldy but also because data warehousing structures, such as star-schema or complex hierarchical structures, are distinctly different from the data structures that these machine learning protocols are generally designed to rely on. More specifically, a number of machine learning protocols commonly used by data scientists to generate predictive models rely on calls to data stored in a tabular format or as a comma-delineated list. As such, data which is warehoused in a complex data structure, such as a star-schema, must first be converted to a table format or must be otherwise extracted from the data structure with a specialized data call. Additionally, as the high degree of fidelity maintained in the warehouse data may add complexity without providing additional, useful details which would affect the predictive model, the extraction process may be designed to be lossy as to extract only the features which are impactful. Performing such operations for each predictive model on a case-by-case basis can be a time and resource intensive project, particularly as reliance on predictive modeling continues to increase. Processing calls for warehoused data into active memory each time a model is run can take up a significant portion of the total processor load of the model, using up CPU time.

Further, representing warehoused data only as a static table is valuable but limiting, as it does not allow for the models to take advantage of updates in the warehoused data. This is a particular disadvantage for predictive modeling, since comparison of predicted outcomes to updates in the data can be useful in verifying the veracity of the predictive models. Additionally, after the veracity of a model is demonstrated, the greatest value of that model will likely come from applying it to updated information to make future predictions.

Pulling data from the data warehouse or distributed big data systems, such as Adobe Hadoop®, into the predictive models generally requires customized extraction procedures, requiring an enormous engineering effort to implement. Such tailored solutions require an intimate knowledge of both the data structures and the predictive models. As such, they are generally the result of an exhaustive collaborative effort between the software engineers and the data scientists. Additionally, as the models develop, the demands for features may change, so the collaborative effort continues through all stages of development.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

At a high level, the present disclosure is directed towards methods, systems, and computer-readable media for populating a feature catalog with features extracted from raw population data stored in a data warehousing structure. The feature catalog may be useful for providing features to predictive modelling applications that would otherwise be incapable of accessing the warehoused data. The data warehousing structure may be a nested, hierarchical structure. Features may be representations of the warehoused data. In some embodiments, features may include simplified projections of more complex warehoused data. The feature catalog may be an organized collection of one or more tables. The catalog may be accessible to predictive modeling applications which would not be able to readily extract data directly from the data warehousing structure. In some embodiments the predictive modeling applications are developed in a rule-based system. The predictive modeling applications may use the feature catalog to generate and improve data models. In some embodiments the predictive modeling applications are developed in a markup language, such as predictive model markup language (PMML), or a structures document, such as JavaScript Object Notation (JSON), or some other XML-based structure, which is both human and machine readable.

After a predictive model is created and verified using features in the feature catalog, the model may be applied against new data to make useful predictions. Updated data may be structured and normalized similar to the warehoused data and a queue of updates may be generated. The rules used to extract features from the warehoused data may be applied to the queue of updates to generate updated features. Predictive models may be applied to these updated features to produce useful predictions.

In one aspect, this disclosure is directed towards a system for converting the form of data contained in a warehoused data structure to be presented to and used in predictive modeling applications. The system comprises a data hub, a reasoning model component, a warehousing component, a rules engine, a feature catalog, and a machine learning component. Though these components are discussed as distinct separate components, each corresponding to a separate specialized computing device, a person having skill in the art of will recognize that it would be possible to combine some or all of these components into a single special-purpose computing device.

The data hub may be configured to receive a first set of raw population data. The first set of raw population data may be associated with a plurality of individuals. Each of the plurality of individuals may be associated with at least one of a plurality of electronic records. At least a portion of the first set of raw population data may comprise logically equivalent data.

The reasoning model component may be configured to perform a transformation on raw population data to generate normalized data. The term transformation, as used herein, comprises identifying and correlating the logically equivalent data.

The warehousing component may be configured to host normalized population data in a data warehousing structure. In some embodiments, the data warehousing structure may be a nested, hierarchical structure, such as a star schema data structure.

The rules engine may be configured to extract a feature set from the normalized population data. In some embodiments, the extraction process may be lossy, such that the resulting feature set is a simplified projection of the raw population data.

The feature catalog may be configured to host the feature set extracted from the normalized population data and represent the feature set in a tabular or comma-delineated data format.

The machine learning component may be configured to run a first predictive model against the features hosted in the feature catalog and generate a prediction. The first predictive model may comprise a set of instructions formatted in a markup language, such as predictive model markup language (PMML). The machine learning component may be configured to run any number of predictive models. In some embodiments, different predictive models may rely upon the same feature catalog. In other embodiments, each different predictive model may rely upon a different feature catalog. In yet other embodiments, predictive models may rely on a combination of feature catalogs, using some features from a first feature catalog and other features from a second feature catalog. In some embodiments, feature catalogs may be specialized; containing only data which is categorically correlated. The machine learning component may apply predictive models to features hosted in a feature catalog to generate predictions of a future outcome. In some embodiments, these predictions may take the form of a risk score.

Some embodiments of the present disclosure may include a display component configured to route the predictions to a service. In some embodiments, the display component may be configured to route the predictions to an electronic record. In other embodiments, the display component may alternatively or additionally be configured to route predictions to another system component or to an external service.

In another aspect, the present disclosure is directed to a method of producing a feature catalog for use with predictive modeling applications across a wide variety of settings. The method may comprise receiving a first set of raw population data. In some instances, a portion of the raw population data may include logically equivalent data. The term "logically equivalent data" is used herein to refer to data which represents a single parameter in at least a plurality of representations. The method may further comprise applying a first set of rule-based algorithms to the first set of raw population data to generate a first set of normalized population data. The normalization rules may be a set of rules-based algorithms configured to identify and correlate the logically equivalent data. The method may further comprise warehousing the set of normalized population data in a data warehousing structure. The method may further comprise applying feature rules to the normalized population data in order to extract a set of features. The feature rules may be another set of rule-based algorithms. The method may further comprise populating at least one feature catalog with the features. The features may be represented in a tabular or comma-delineated data format.

In yet another aspect, the present disclosure is directed to a method of hosting a predictive model. The method may comprise receiving updated raw population data at a data hub. The method may further comprise normalizing the updated raw population data to generate a queue of updates. Normalizing may comprise structurally correlating the updated raw population data to correspond with the structure of data stored in a data warehouse. The method may further comprise receiving a call for a set of features from a machine learning component. The features called for may have been previously generated by applying feature rules to the warehoused data. The method may further comprise analyzing the feature rules which were responsible for generating the features originally to determine precursor data, wherein precursor data refers to warehoused data relied upon in generating the features. Some portion of the queue of updates may correspond to the precursor data. The method may further comprise applying features rules responsible for generating the features being called for to the queue of updates to generate updated features. The method may further comprise returning the updated features to the machine learning component in response to the call for features. The method may further comprise applying the updated features to a predicative model to generate a prediction and reporting the prediction to a service or an electronic record.

BRIEF DESCRIPTION OF THE DRAWINGS

Some embodiments are described in detail below with reference to the attached drawings

DETAILED DESCRIPTION

The subject matter of aspects of the present disclosure is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present disclosure are directed to methods, systems, and computer-readable media for producing and maintaining a feature catalog populated with data features extracted from a warehousing data structure. The feature catalog may be structured to be compatible with one or more predictive modeling applications.

Figure 1:
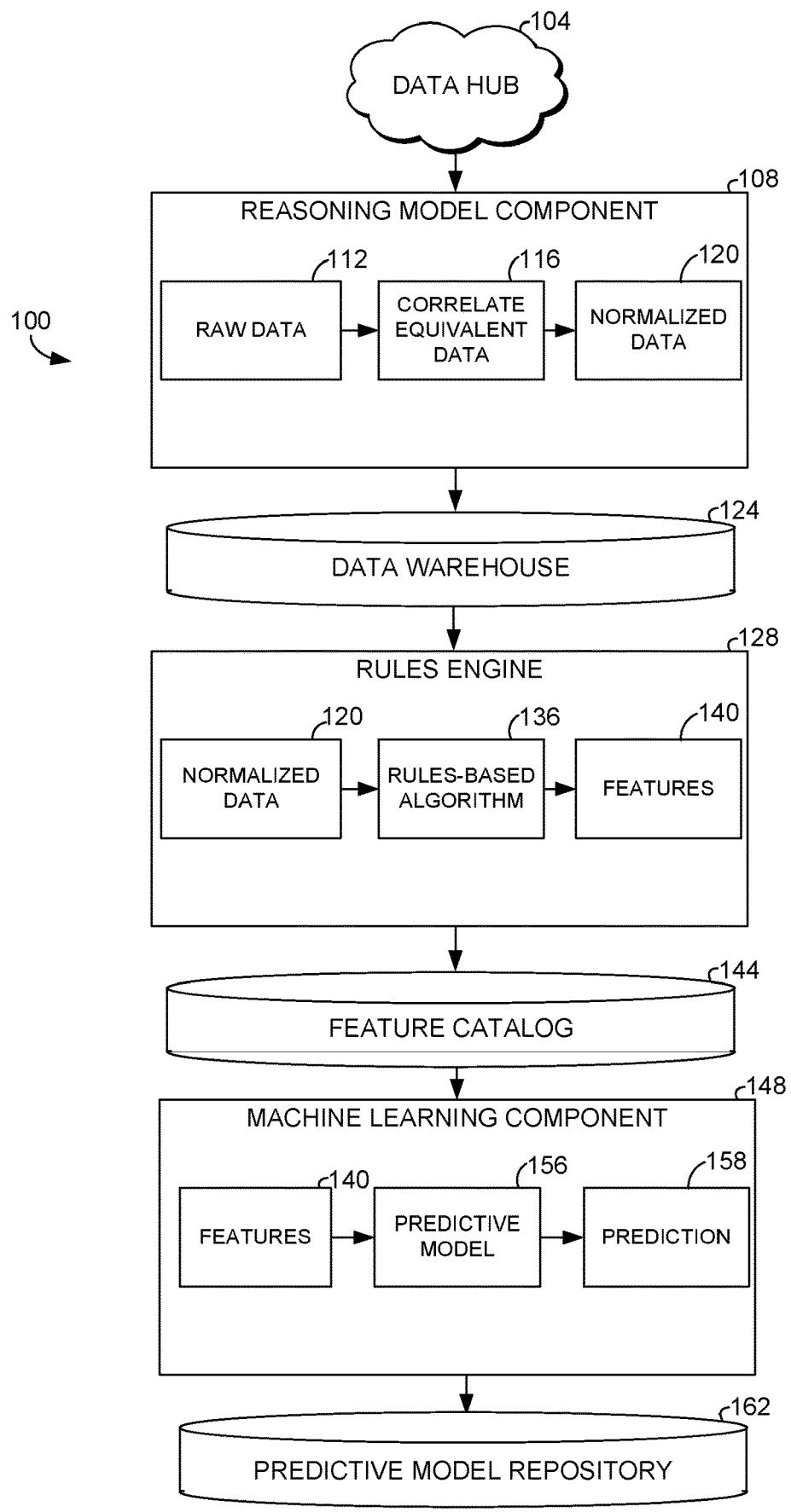
FIGS. 1-2 depict exemplary system architectures suitable to implement embodiments of the present disclosure.

In FIG. 1, a computer system architecture for presenting stored data for use in a predictive modeling environment, generally labeled with the numeral 100, is shown. Though it may be possible to assemble computer system architecture 100 from general purpose computing devices, the ordered combination of system architecture 100, taken as a whole, serves to direct the constituent computing devices to a new and useful end. Additionally, though these components are discussed as distinct separate components, each corresponding to a separate specialized computing device, a person having skill in the art of will recognize that it would be possible to combine some or all of these components into a single special-purpose computing device Data hub 104 is configured to receive a first set of raw population data 112. Raw population data 112 may be received from multiple different sources. Data hub 104 may be a scalable, highly parallel system capable of distributed storage and distributed processing of very large data sets on computer clusters. A computer cluster is a plurality of computing devices networked together to work together and function essentially as a single machine. The computing devices may be networked together directly, over a Local Area Network or Wireless Area Network, or indirectly networked over an Intranet or over the Internet. Examples of systems which may meet these criteria include Apache Hadoop®.

Raw population data 112 may comprise a plurality of individual electronic records. Each electronic record may be associated with an individual, such as an individual customer, an individual test site, or an individual patient in a medical context. In some embodiments, more than one record may be associated with a single individual.

The specific configuration in which the bits of raw population data 112 appears on a disk can be referred to as the physical model of the data. Raw data maintained in the physical model can be highly complicated and difficult to search or navigate, but retains the highest fidelity to the data source. In the physical model, raw population data 112 may include logically equivalent data. Data is logically equivalent if it represents a measurement of a single parameter in multiple different ways. There may be different representations of logically equivalent data within a single record or there may be logically equivalent data across multiple records in the population data.

Reasoning model component 108 is configured to perform a transformation on the raw population data 112 to generate normalized population data 120. Normalized population data 120 is semi-structured raw population data which retains a high degree of fidelity to the raw population data 112 from which it is sourced, but it categorically associated with similar data fields extant in the electronic records which make up the raw population data 112. The reasoning model refers to a standardized model for correlating disparate representations of logically equivalent data within an electronic record or across the raw population data 112. The reasoning model is generating by applying a set of rules to the physical model, i.e. to raw population data 112. These rules identify and correlate the differing representations of logically equivalent data 116. For instance, concept mapping may be applied; changing disparate code values or notational systems into a common form and implementing structural changes driven by rules. Examples of concept mapping systems may include Unified Medical Language System (UMLS) as well as purpose-build concept modeling systems. In some embodiments, for each of a plurality of possible representations of a parameter there may be a separate rule to apply.

The normalized population data 120 is then stored in data warehouse 124. A data warehouse is a data store organized for deep storage of data. Data warehouse 124 may be configured to host normalized population data 120 in a data warehousing structure. Data warehousing structures may be organized in highly nested, hierarchical structures which permit simple access for common queries and storage of normalized population data 120 with a high degree of fidelity, such as star-schema style data structure or a snowflake schema data structure. Such data structures are used widely for their simplicity and effectiveness at handling simple queries, but these architectures prove to be a hindrance when developing particular types of predictive models, as hierarchical data structures cannot easily respond to the types of inquiries generated by predictive models and the applications used to develop them.

Rules engine 128 may be configured to extract features 140 from the normalized population data 120. The term "feature" has the definition used in data science. In some instances, a feature may be a direct representation of normalized data. However, in other instances, a feature may be an abstraction from the source data. Features 140 may be extracted from the normalized population data 120 by applying a set of rules-based algorithms 136. A rules-based system allows for machine readable instructions which are more easily interpreted by a human reader. This allows for information to be interpreted in more useful ways. In some embodiments, the application of these rules-based algorithms 136 may result in a lossy process, which generates features 140 having less fidelity to the source data than the normalized population data 120. In this way, features 140 may represent a simplified projection of the normalized population data 120. A simplified projection may be a representation of source data, such as normalized population data 120, which carries less specificity than the source data (e.g., the raw data 112). In some cases, a simplified projection may be, for instance, a True or False statement with regards to whether a value in the data is above a particular threshold value. Though there is generally value in warehousing the normalized population data 120 at a high level of fidelity, such a high level of fidelity is not generally required for a particular predictive model, and therefore need not be maintained within features 140.

Feature catalog 144 is configured to host features 140. A feature catalog may take the form of an organized collection of one or more data tables. Each table may contain a set of related features. In some embodiments, feature catalog 144 may be physically housed in memory or stored to disk in a location geographically separate from data warehouse 124 and data hub 104. In other embodiments of the present disclosure, feature catalog 144 and data warehouse 124, as well as various other components of system 100, may be housed in the same location. In some embodiments, various components of the system 100, including data warehouse 124 and feature catalog 144, may be housed within data hub 104. Such embodiments may benefit from improved efficiency over embodiments where the various components are geographically dispersed.

Machine learning component 148 may be configured to run predictive model 156 against features 140 hosted in feature catalog 144. Predictive modeling leverages statistics to predict outcomes. For example, statistical techniques such as multiple algorithms, linear regression, partial least squares and logistic regression, neural networks, genetic algorithms or other machine learning procedures may be applied to data features for a variety of patients. The term predictive modeling is closely tied to machine learning, and in many cases, the terms may be used interchangeably. Popular machine learning tools and libraries include R and scikit-learn, SAS, and several others. Many of these tools are designed to require tabular data as input. As such, these tools can make use of the data stored in feature catalog 144, whereas they would not be able to make use of the normalized population data 120 hosted in the data warehouse 124. Running predictive model 156 against the features 140 may result in the generation of predictions 158.

Machine learning and predictive modeling goes beyond comparing old and new data based on a set of rules or sorting data, in that the machine learning process identifies correlations within the data that are unknown to the human user. As such, machine learning and predictive modeling systems provide functionality that could not be accomplished by a human being using only pencil and paper and the effort of their own mind. Predictive modeling is inherently tied to computer science in that it refers to leveraging computers to detect patterns in large volumes of data.

Both predictive modeling and machine learning are dependent on the use of at least one digital computing device to be functional. One having skill in the art will realize that the terms 'predictive modeling' and 'machine learning' have little, if any, practical meaning outside of the computer science context and, as such, the technologies are inherently linked to the computer science context.

In some embodiments, machine learning component 148 sends predictive model 156 to be stored in predictive model repository 162. Predictive model 156 may be evaluated based on the accuracy and precision of prediction 158 to determine if predictive model 156 will be retained in predictive model repository 162. Evaluation may include comparing prediction 158 with actual historical outcomes within the electronic records which help make up the normalized population data 120. In some instances, alterations may be made to predictive model 156 and then predictive model 156 will be reapplied to features 140 in order to improve the accuracy of the prediction generated. At which point, predictive model 156, thus improved, may be stored in predictive model repository 162. In other instances, predictive model 156 may be discarded due to the weakness of prediction 158.

Figure 2:
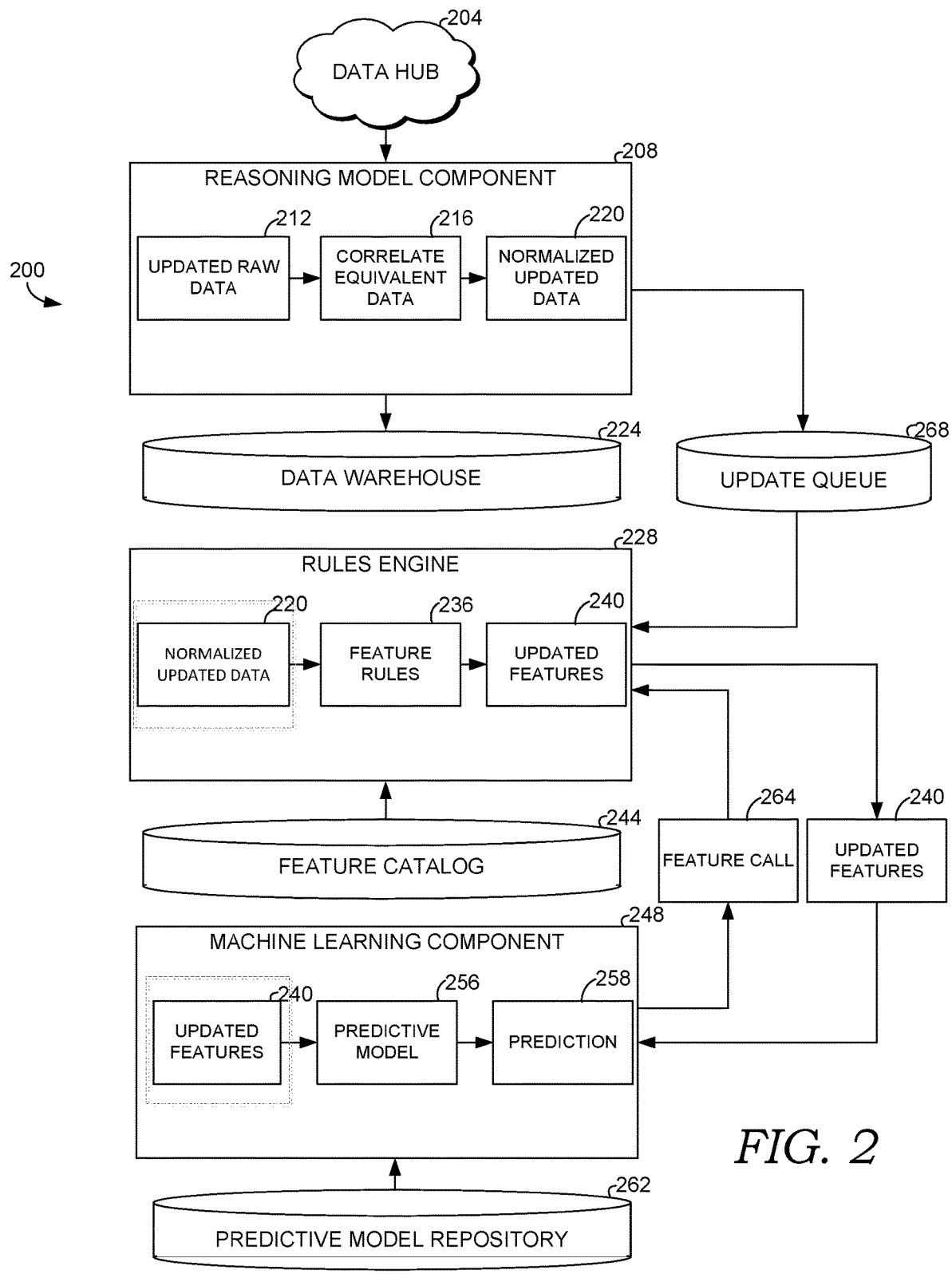

FIG. 2 depicts a computer system architecture for hosting predictive model applications, generally labeled with the numeral 200, is shown. System 200 may correlate to system 100, wherein the initial phase, geared towards populating the feature catalog in order to generate and test predictive models, gives way to a hosting phase, wherein the vetted predictive models are applied to new population data in order to produce valuable predictions.

Data hub 204 functions similarly to data hub 104 and may be configured to receive updated raw population data 212. Reasoning model component 208 corresponds to reasoning model component 108 and may be configured to identify and correlate logically equivalent data 216 within the updated raw population data 212 in order to generate normalized updated population data 220. This normalized population data 220 is organized to form a queue of updates 268. In some embodiments, the normalized updated population data 220 may also be incorporated into data warehouse 224. Data warehouse 224 corresponds to data warehouse 124.

In some embodiments of the present disclosure, machine learning component 248 sends a feature call 264 to rules engine 228. In response, rules engine 228 determines the feature rules 236 responsible for generating the features requested in the feature call 264. Upon identifying the responsible feature rules 236, rules engine 228 analyzes the feature rules 236 to determine the precursor data relied upon by the feature rules 236. The term 'precursor data' is used herein to denote data stored in data warehouse 224, which was initially used in generating the feature now being requested by the feature call 264. In some instances, updates queue 268 contains data which corresponds to the precursor data. In such instances, feature rules 236 are applied to normalized updated data 220 held in the update queue 268 in order to generate updated features 240. This type of just-in-time generation of feature updates tends to reduce the processor demand of hosting predictive models as compared to fully updating the entire feature catalog each time a feature call is generated. The updated features 240 may be sent to machine learning component 248 in response to feature call 264. In some embodiments of the present disclosure, updated features 240 may also be sent to feature catalog 244. In some embodiments, features which do not have corresponding data contained in update queue 268 may be pulled from feature catalog 244.

Machine learning component 248 may be configured to apply predictive model 256 to the updated features 240 in order to generate prediction 258. In some embodiments, predictive model 256 may be pulled from predictive model repository 262. In some embodiments, prediction 258 may be sent to an electronic record. In other embodiments, prediction 258 may, alternatively or additionally, be sent to another component or service.

Figure 3:
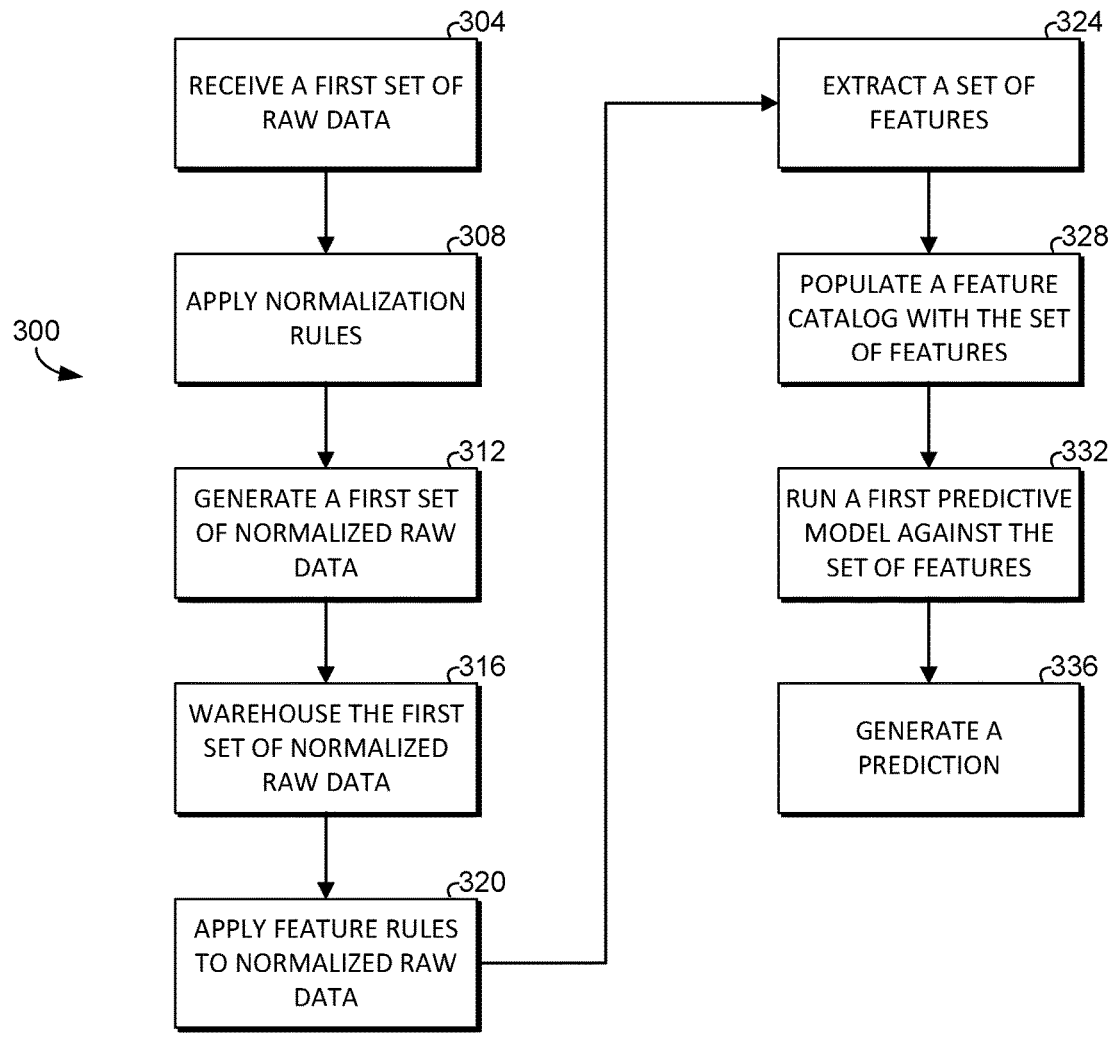
FIGS. 3-4 depict exemplary flow diagrams depicting embodiments of the present disclosure.

Turning now to FIG. 3, a flow diagram is depicted of an exemplary method 300 for producing a feature catalog for use with predictive modeling applications across a wide variety of settings. The method 300 is directly related to the computing system architecture 100 described in respect to FIG. 1. As such, reference will be made to the components of the computing system architecture 100 when describing the method 300.

At step 304, a first set of raw population data is received. This first set of raw population data may be received at data hub 104. In some embodiments, a portion of the raw population may include logically equivalent data representing a single parameter in more than one way. In step 308, normalization rules are applied to the first set of raw population data. The normalization rules may be a set of rules-based algorithms configured to identify and correlate the logically equivalent data. As a result, a first set of normalized population data is generated at step 312. These steps may occur at reasoning model component 108.

At step 316, the first set of normalized population data is warehoused in a data warehousing structure, such as data warehouse 124. At step 320, feature rules are applied to the normalized population data. As a result, a set of features is extracted at step 324. These steps may occur at rules engine 128. The feature rules may be a second set of rules-based algorithms. At step 328, feature catalog 144 is populated with the set of features. The features are represented in feature catalog 144 as tabular or comma-delineated data.

In some embodiments, the method continues to step 332, wherein a first predictive model is run against the set of features in feature catalog 144. As a result, the first predictive model may generate a prediction at step 336. These steps may occur at machine learning component 148.

Figure 4:
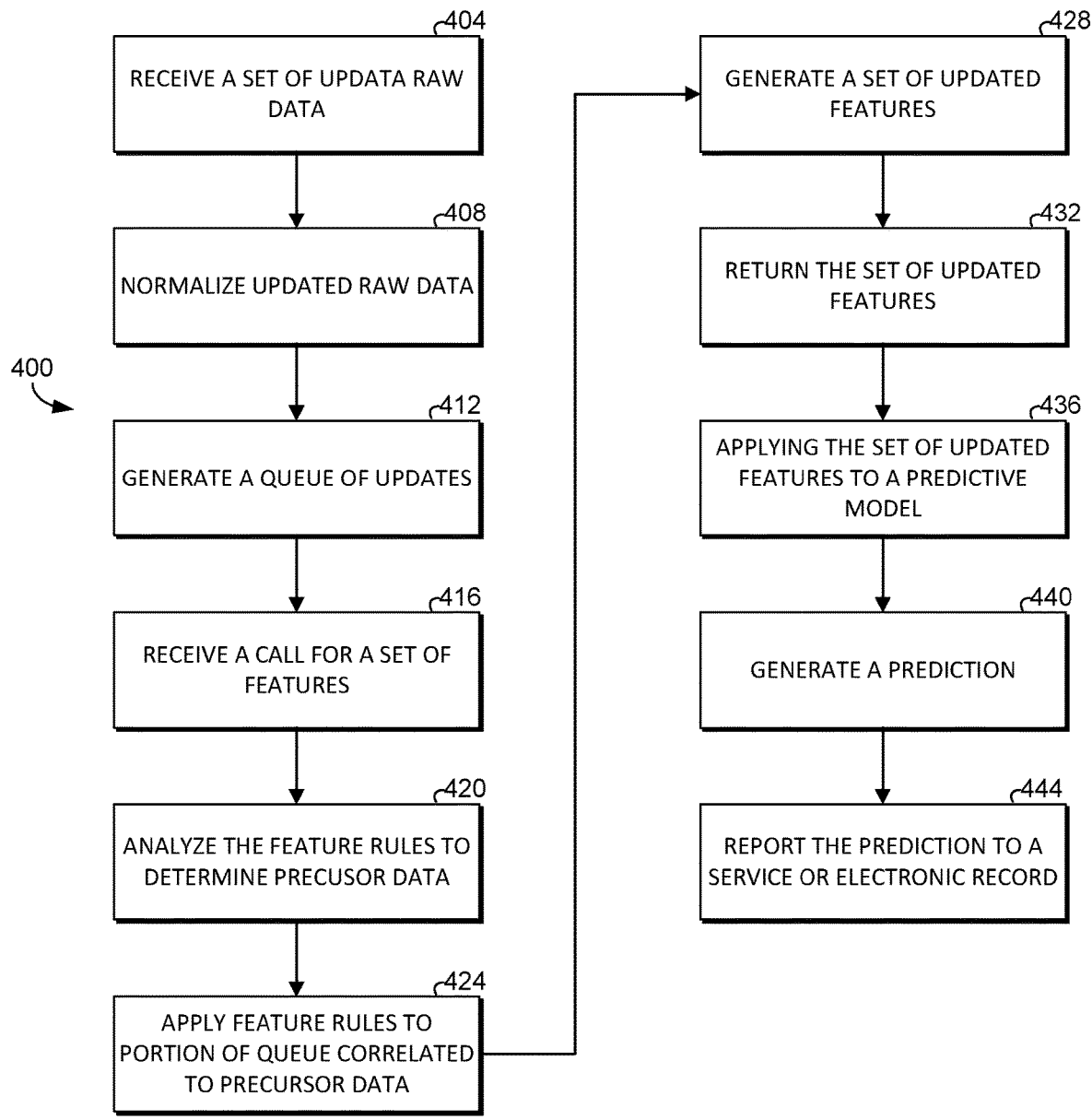

FIG. 4 depicts a flow diagram of an exemplary method 400 for hosting a predictive model. The method 400 is directly related to the computing system architecture 200 described in respect to FIG. 2. As such, reference will be made to the components of the computing system architecture 200 when describing the method 400.

In step 404, a set of updated raw population data 212 is received. This step may occur at data hub 204. At step 408, the updated raw population data 212 is normalized. This step may occur at reasoning model component 208. Normalization may include organizing the updated raw population data 212 into a data structure which mirrors the structure of data warehouse 224. Normalized updated population 220 is then used to generate a queue of updates 268 at step 412.

At step 416, machine learning component 248 generates a feature call 264, requesting a set of features and the feature call 264 is received by rules engine 228. At step 420, rules engine 228 determines the feature rules 236 responsible for generating the features requested in feature call 264. The responsible feature rules 236 are then analyzed to determine the precursor data relied upon by the feature rules 236. Precursor data refers to the portion of the warehoused data relied upon initially to generate the features requested in feature call 264. In some instances, a portion of the precursor data may correspond to a portion of the queue of updates 268. In other words, there may be new data incorporated into the queue of updates 268 which represents an update to the precursor data.

At step 424, the feature rules 236 responsible for generating the requested features in feature call 264 are applied to the queue of updates 268. As a result, a set of updated features 240 is generated at step 428. At step 432, the updated features 240 are returned. In some instances, there may not be an updated feature for every feature requested in feature call 264. In such instances, features which cannot be generated by applying feature rules 236 to the queue of updates 268 are, instead, pulled from the feature catalog 244.

At step 436, the updated features 240 are applied to a predictive model 256. As a result, a prediction is generated at step 440. These steps may occur at machine learning component 248. At step 444, the prediction 258 is reported to a service or an electronic record.

One exemplary application of this disclosure is in the parallel fields of medical records management and predictive medicine. Embodiments of the present disclosure address challenges particular to technical environments, such as those computer architectures discussed in this disclosure, as these computer architectures are applied in the health care records management and predictive modeling context.

Software engineers working in medical records management maintain the data structure which store population medical data. Population medical data may comprise historical data for a variety of patients, which could be utilized by predictive models and may be warehoused in relational databases. The historical data may include ICD-9 admission codes for each of the patients, ages of each of the patients, location or region for each of the patients, admitting diagnoses codes, working diagnoses codes, actual length of hospital stay, ordered procedures, treating physician names, outcomes and other clinical data related to treatment of the patient. This data may come in from various sources and may include information from, for example, a hospital, a physician's office, a health information exchange, an urgent care clinic, and the like. Healthcare data may include, but is not limited to, information that describes various aspects of the patient state, including patient vitals, lab results, biometrics, medication orders, diagnosis codes, condition codes, clinical orders, claims, patient demographic information, patient history, patient images, participation in wellness programs, and a variety of other information. Laboratory and biometric data collected may include age, gender, lipids (HDL, LDL, and triglycerides), body mass index (BMI), glucose/HbA1c, and the like.

As in other industries, software engineers are generally tasked with ensuring that there is support for the demands placed on these data structures. Those demands include receiving and responding to queries, updating existing electronic health records (EHRs), adding new EHRs, and supporting integration with other software and systems.

EHR are designed to be understood and interpreted by human observers and may include peculiarities in formatting which are not particularly troubling for a human to interpret. A human observer of a conventional patient file would be able to read a file and determine which information in the file is relevant. For instance, a human observer could scan through a file to determine whether a patient has been prescribed warfarin. While the formatting of the document may make it easier for a human observer to search, a human observe is capable to find relevant information, if present, regardless of the formatting of the document. A computer system is not generally capable of deciphering context clues which would be obvious to a human observer, however computer systems are capable of processing and analyzing data in ways that humans cannot. As such, enabling a computer system to contextualize data contained in an EHR the same way a human might presents a technological problem which requires technological solution.

Data scientists develop the models which applies the population medical data. These models may depend on any number of covariates relating to patient characteristics or diagnoses or treatment histories, and varies widely depending on what the modeling is meant to predict. For instance, if data scientists wanted to look for predictive factors which contribute to a population member having an increased risk for diabetes, it might be that only a small number of field determine that increased risk. For instance, the risk for diabetes might be determined based on something in the order of dozens of lab results. However, it is not always obvious from the outset which data features will be relevant for a highly effective predictive model.

In application, numerous items of data including, but not limited to, demographic information, medical condition information, wellness program information, medical insurance and the like, may be relevant to a predictive model. Covariates may include age categories, gender, medical history of child birth, heart attack, chronic heart failure, diagnoses of hypertension, dyslipidemia, back pain, obesity, peripheral vascular disease, cerebrovascular disease, pulmonary disease, rheumatologic disease, peptic ulcer disease, liver disease, diabetes, Hemiplegia, paraplegia, cancer, AIDS, and depression/anxiety.

By leveraging machine learning and predictive modeling techniques, healthcare patient population data warehoused in data stores can be leveraged to greater affect.

In the medical context, raw population medical data may be received at a data hub corresponding to a plurality of EHRs which, in turn, correspond to a plurality of patients. The raw population data may comprise logically equivalent data. For example, data relating to a patient's albumin level may be represented in 30 different ways, however, as all these representations relate to a single parameter (albumin level), all of these representations are logically equivalent.

The reasoning model component might transform the various representations of logically equivalent data by identifying and correlating them into a single category by applying rules-based algorithms. Through application of these algorithms, the 30 different possible representations of albumin level within an EHR may be correlated and recognized as relating to the same data. All the albumin measurements may then be grouped and warehoused within the patient's EHR under the broad heading 'medical results'. Likewise, assuming a patient has been prescribed warfarin, this may be broadly placed within the category of "consumables" within the patients EHR. This allows raw patient data to be normalized.

EHRs may be stored in this normalized form within a nested, hierarchical data structure, such as a star schema data store. Such a data structure is preferable for storing EHRs, as EHRs are regularly updated with new entries and are generally searched with queries by patient as opposed to, for instance, a query by prescription or by test result.

A rules engine may then extract features from the normalized population medical data. Features may be a direct representation of normalized data, such as an exact representation of a patient's albumin level, or an abstraction. For example, a series of different measurements of albumin level taken over a period of months or years and the corresponding date and time information relating to that albumin level measurement may be represented as a 10-week moving average of the albumin level. This moving average would be a simplified projection of the measurement data, as it represents the source data but does not carry the granular specificity of the source data. In yet another instance, a feature may return a Boolean expression regarding whether some portion of the normalized data satisfies some conditional statement. For example, a feature might present "TRUE" if the EHR shows that the patient is being prescribed Warfarin.

The features thus extracted may be stored in a single table, in multiple tables in a single feature catalog, or they may be stored in multiple feature catalogs. For instance, one table might include medications, with a column for each medication a person has been prescribed. In other instances, a table might include sets of problems, allergies, conditions, procedures, lab results, or other sets of features which may be categorically associated.

These feature catalogs may be used in machine learning components in order to produce predictive models. These predictive models may be designed to predict the likelihood of a future diagnosis based off of features extracted from raw medical population data. Successful models may then be applied to updates in a patient's EHR in order to evaluate that patient's risk, for example, of being diagnosed with diabetes. A patient's risk might be represented as a risk score. This risk score may be saved to that patient's EHR. Alternatively, or in addition, that risk score might be forwarded to a service, such as a wellness program for which the patient qualifies based on the risk score.

Figure 5:
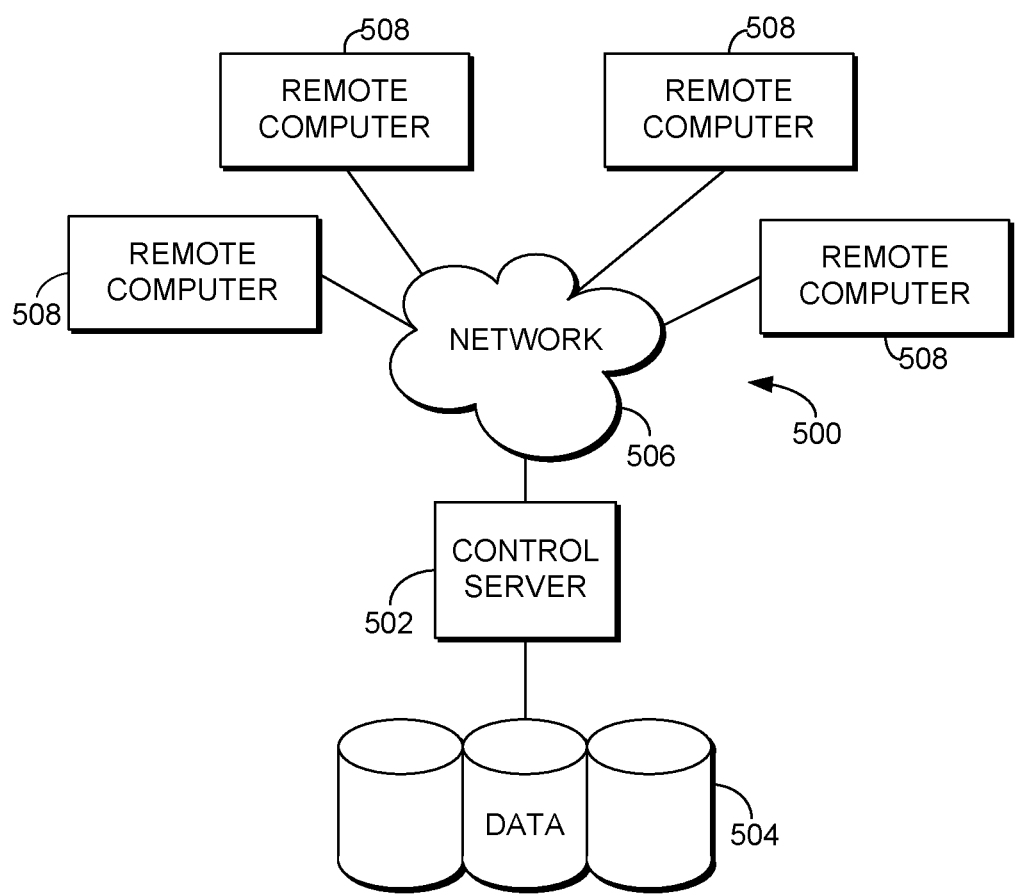
FIG. 5 is a block diagram of an exemplary computing environment suitable to implement embodiments of the present disclosure.

An exemplary computing environment suitable for use in implementing embodiments of the present disclosure is described below. FIG. 5 is an exemplary computing environment (e.g., medical-information computing-system environment) with which embodiments of the present disclosure may be implemented. The computing environment is illustrated and designated generally as reference numeral 500. The computing environment 500 is merely an example of one suitable computing environment and is not intended to suggest any limitation as to the scope of use or functionality of the disclosure. Neither should the computing environment 500 be interpreted as having any dependency or requirement relating to any single component or combination of components illustrated therein.

Aspects of present disclosure are directed to a special computing system that can leverage well-known computing system environments or configurations. Examples of well-known computing systems, environments, and/or configurations that might be suitable for use with the present disclosure include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present disclosure might be described in the context of computer-executable instructions, such as program modules, being executed by a computer. Exemplary program modules comprise routines, programs, objects, components, and data structures that perform particular tasks or implement particular abstract data types. The present disclosure might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 5, the computing environment 500 comprises a computing device in the form of a control server 502. Exemplary components of the control server 502 comprise a processing unit, internal system memory, and a suitable system bus for coupling various system components, including data store 504, with the control server 502. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 502 typically includes therein, or has access to, a variety of non-transitory computer-readable media. Computer-readable media can be any available media that might be accessed by control server 502, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 502. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 502 might operate in a computer network 506 using logical connections to one or more remote computers 508. Remote computers 508 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 508 might also be physically located in nontraditional medical care environments so that the entire healthcare community might be capable of integration on the network. The remote computers 508 might be personal computers, servers, routers, network PCs, peer devices, other common network nodes, or the like and might comprise some or all of the elements described above in relation to the control server 502. The devices can be personal digital assistants or other like devices.

Computer networks 506 comprise local area networks (LANs) and/or wide area networks (WANs). Such networking environments are commonplace in offices, enterprise-wide computer networks, intranets, and the Internet. When utilized in a WAN networking environment, the control server 502 might comprise a modem or other means for establishing communications over the WAN, such as the Internet. In a networking environment, program modules or portions thereof might be stored in association with the control server 502, the data store 504, or any of the remote computers 508. For example, various application programs may reside on the memory associated with any one or more of the remote computers 508. It will be appreciated by those of ordinary skill in the art that the network connections shown are exemplary and other means of establishing a communications link between the computers (e.g., control server 502 and remote computers 508) might be utilized.

In operation, an organization might enter commands and information into the control server 502 or convey the commands and information to the control server 502 via one or more of the remote computers 508 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote healthcare device to the control server 502. In addition to a monitor, the control server 502 and/or remote computers 508 might comprise other peripheral output devices, such as speakers and a printer.

Although many other internal components of the control server 502 and the remote computers 508 are not shown, such components and their interconnection are well known. Accordingly, additional details concerning the internal construction of the control server 502 and the remote computers 508 are not further disclosed herein.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. A system for presenting stored data for use in a predictive modeling environment comprising:
   a data hub configured to:
      receive a first set of raw population data wherein the raw population data comprises a plurality of patient electronic health records (EHR), wherein the first set of raw population data is associated with a plurality of individuals;
      wherein each of the plurality of individuals is associated with at least one of the plurality of electronic health records; and
      wherein at least a portion of the first set of raw population data comprises logically equivalent data, wherein the logically equivalent data is data which represents a single parameter of the plurality of patient EHR in at least a plurality of representations, each of the plurality of representations is representative of the single parameter;
   a reasoning model component configured to perform a transformation on the raw population data, including the logically equivalent data, to generate a normalized population data of the single parameter, wherein the normalized population data is in one of the plurality of representations;
   wherein the transformation comprises identifying and correlating the logically equivalent data to the single parameter;
   a data warehouse configured to host the normalized population data in a data warehousing structure;
   a rules engine configured to extract a feature set from the normalized population data wherein the feature set comprises an exact representation of the logically equivalent data or an abstraction of the logically equivalent data which represents the single parameter of the plurality of patient EHR in at least the plurality of representations;
   a feature catalog configured to host the feature set extracted from the normalized population data and represent the feature set in a tabular format;
   a machine learning component configured to run a first predictive model against the feature set hosted in the feature catalog and generate a prediction;
   wherein the first predictive model comprises a set of instructions; and
   a display component configured to route the prediction to a service.

2. The system of claim 1, wherein the first predictive model is formatted in a markup language.

3. The system of claim 2, wherein the markup language is predictive model markup language (PMML).

4. The system of claim 1, wherein the first predictive model is formatted in a structured document that is human and machine readable.

5. The system of claim 1, wherein the data warehousing structure comprises a nested, hierarchical structure.

6. The system of claim 5, wherein the data warehousing structure further comprises a star schema data structure.

7. The system of claim 1, wherein the rules engine is further configured to extract the feature set by a lossy process and wherein the feature set comprises a simplified projection of the normalized population data.

8. The system of claim 1, wherein the display component is configured to route the prediction to an electronic record.

9. The system of claim 1, wherein the machine learning component is further configured to run a second predictive model.

10. The system of claim 1, wherein at least the first predictive model is stored in a predictive model repository.

11. A method for producing a feature catalog for use with predictive modeling applications across a wide variety of settings, the method comprising:
    receiving a first set of raw population data wherein the raw population data comprises a plurality of patient electronic health records (EHR);
    wherein at least a portion of the raw population data includes logically equivalent data;
    wherein logically equivalent data represents a single parameter of the plurality of patient EHR in at least a plurality of representations each of the plurality of representations is representative of the single parameter;
    applying normalization rules to the first set of raw population data including the logically equivalent data, to generate a first set of a normalized population data of the single parameter, wherein the normalized population data is in one of the plurality of representations;
    wherein the normalization rules are a first set of rules-based algorithms configured to identify and correlate the logically equivalent data to the single parameter;
    warehousing the first set of the normalized population data in a data warehousing structure;
    applying a feature rules to the normalized population data in order to extract a set of features wherein the feature rules are a second set of rules-based algorithms, wherein the set of features comprises an abstraction of the logically equivalent data which represents the single parameter of the plurality of patient EHR in at least the plurality of representations; and
    populating at least a first feature catalog with at least a first portion of the set of features; wherein the set of features are represented in a tabular format.

12. The method of claim 11, further comprising:
    running a first predictive model against the set of features; and generating a prediction.

13. The method of claim 11, further comprising populating at least a second feature catalog with at least a second portion of the set of features.

14. The method of claim 11, wherein the raw population data comprises the plurality of electronic health records pertaining to a plurality of individual patients.

15. A method of hosting a predictive model, the method comprising:
    receiving, at a data hub, a set of updated raw population data comprising a plurality of electronic health records (EHR), and wherein the raw population data comprises logically equivalent data which represents a single parameter of the plurality of EHR in at least a plurality of representations each of the plurality of representations is representative of the single parameter;
    normalizing the updated raw population data, including the logically equivalent data, to generate a queue of updates of the single parameter, wherein the normalized population data is in one of the plurality of representations;
    wherein normalizing comprises structurally correlating the updated raw population data with warehoused data to the single parameter, wherein warehoused data comprises data warehoused in a data warehouse;

receiving, from a machine learning component, a call for a set of features, wherein the set of features was previously generated by applying a feature rules to the warehoused data;

analyzing the feature rules responsible for generating the set of features to determine a precursor data, wherein the precursor data is a portion of the warehoused data relied upon to generate the set of features;

wherein at least a portion of the queue of updates is correlated to the precursor data;

applying the feature rules responsible for generating the set of features to the portion of the queue of updates correlated to the precursor data in order to generate a set of updated features, and wherein the set of features comprises an abstraction of the logically equivalent data which represents the single parameter of the plurality of patient EHR in at least the plurality of representations;

in response to the call for the set of features, returning at least the set of updated features;

at the machine learning component, applying the at least the set of updated features to a predictive model to generate a prediction; and reporting the prediction to a service or an electronic record.

16. The method of claim 15, wherein the call for the set of features comprises at least one feature for which there is no updated feature and wherein the at least one feature is received from a feature catalog.

17. The method of claim 15, wherein the prediction is a risk score or a diagnosis.

18. The method of claim 15, wherein the prediction is returned to the plurality of electronic health records (EHR).

19. The method of claim 15, wherein at least one of the set of features requested in the feature call is related to a medication prescribed to a patient.

* * * * *